US008292435B2

United States Patent
Kanazawa (10) Patent No.: US 8,292,435 B2
(45) Date of Patent: Oct. 23, 2012

(54) OPTOMETRIC APPARATUS (75) Inventor: Yuichiro Kanazawa, Okazaki (JP)

(73) Assignee: Nidek Co., Ltd., Gamagori (JP)

( * ) Notice: Subject to any disclaimer, the term of this patent is extended or adjusted under 35 U.S.C. 154(b) by 266 days.

(21) Appl. No.: 12/874,410

(22) Filed: Sep. 2, 2010

(65) Prior Publication Data

US 2011/0075099 A1 Mar. 31, 2011

(30) Foreign Application Priority Data

Sep. 29, 2009 (JP) ................................. 2009-225529

(51) Int. Cl.
*A61B 3/02* (2006.01)
*A61B 3/08* (2006.01)

(52) U.S. Cl. ........ 351/232; 351/201; 351/233; 351/237; 351/240; 351/244

(58) Field of Classification Search .................. 351/232, 351/240, 244, 245
See application file for complete search history.

(56) References Cited

U.S. PATENT DOCUMENTS

| 5,331,358 A | | 7/1994 | Schurle et al. | |
| 5,444,504 A | * | 8/1995 | Kobayashi et al. | ........... 351/237 |
| 5,638,082 A | * | 6/1997 | Grimm | ............................. 345/6 |
| 7,568,801 B2 | | 8/2009 | Inagaki et al. | |
| 7,607,778 B2 | * | 10/2009 | Oda | ............................. 351/240 |
| 2004/0184001 A1 | | 9/2004 | Terabe | |
| 2009/0244486 A1 | * | 10/2009 | Oda | ............................. 351/240 |

FOREIGN PATENT DOCUMENTS

EP 2 014 222 A1 1/2009
JP A-2008-264262 11/2008

OTHER PUBLICATIONS

Extended Search Report issued in European Application No. EP 10 17 8201 dated Jan. 28, 2011.

* cited by examiner

*Primary Examiner* — Jordan Schwartz
(74) *Attorney, Agent, or Firm* — Oliff & Berridge, PLC (57) ABSTRACT

An optometric apparatus for a subjective binocular visual performance test includes right and left test units including right and left housings, a plurality of optical elements disposed in the right and left housings, right and left test windows provided to the housings, in which desired optical elements selected from the optical elements are to be placed and through the selected optical elements, an optotype is presented to examinee's right and left eyes by an optotype presenting apparatus, right and left polarization plates having polarization axes perpendicular to each other and arranged to be placed in the test windows, and right and left protective covers arranged to be placed in the test windows at a side facing the optotype presenting apparatus and having polarization optical characteristics of changing circularly polarized light that passes through the right and left protective covers into linearly polarized light having polarization axes perpendicular to each other.

6 Claims, 7 Drawing Sheets

OPTOMETRIC APPARATUS

BACKGROUND OF THE INVENTION

1. Field of the Invention

The present invention relates to an optometric apparatus for subjectively testing (measuring) visual performance of an examinee's eye such as refractive power.

2. Description of Related Art

Conventionally, there is known an optometric apparatus called a refractor and a phoropter that is arranged to place an optical element in front of an examinee's eye, show to the eye an optotype presented in front of the optical element through it, and based on the visibility of the optotype, subjectively test (measure) visual performance of the eye such as refractive power and binocular visual performance. In addition, there is known an optotype presenting apparatus including a liquid crystal display, by which the optotype is presented. In a binocular vision test using these kinds of optometric apparatus and optotype presenting apparatus, an optotype for a binocular vision test is presented by an apparatus including a polarization optical member that has polarization axes perpendicular to each other and is attached in front of the liquid crystal display, and a polarization optical element compatible with linearly polarized light is placed in front of a right eye and a left eye of an examinee (see U.S. Pat. No. 7,568,801 corresponding to Japanese Patent Application Laid-Open Publication No. 2008-264262). Another example of the optotype presenting apparatus includes an apparatus in which circularly polarized light is used instead of linearly polarized light, and in a binocular vision test using this kind of optotype presenting apparatus, a polarization optical element compatible with circularly polarized light is placed in front of a right eye and a left eye of an examinee.

In order to have the optometric apparatus compatible with both the optotype presenting apparatus in which the linearly polarized light is used and the optotype presenting apparatus in which the circularly polarized light is used, it is necessary for the optometric apparatus to include both of the polarization optical element compatible with the linearly polarized light and the polarization optical element compatible with the circularly polarized light. However, including both the polarization optical elements causes upsizing of the optometric apparatus and an increase in cost.

SUMMARY OF THE INVENTION

An object of the invention is to provide an optometric apparatus for a binocular vision test that is easily compatible with both of an optotype presenting apparatus in which linearly polarized light is used, and an optotype presenting apparatus in which circularly polarized light is used.

To achieve the objects and in accordance with the purpose of the present invention, an optometric apparatus for a subjective binocular visual performance test includes right and left test units including right and left housings, a plurality of optical elements disposed in each of the right and left housings, right and left test windows provided respectively to the right and left housings, in which desired optical elements selected from the optical elements are to be placed and through the selected optical elements, an optotype is presented to examinee's right and left eyes by an optotype presenting apparatus, right and left polarization plates having polarization axes perpendicular to each other and arranged to be placed respectively in the right and left test windows, and right and left protective covers arranged to be placed respectively in the right and left test windows at a side facing the optotype presenting apparatus and having polarization optical characteristics of changing circularly polarized light that passes through the right and left protective covers into linearly polarized light having polarization axes perpendicular to each other.

Additional objects and advantages of the invention are set forth in the description which follows, are obvious from the description, or may be learned by practicing the invention. The objects and advantages of the invention may be realized and attained by the optometric apparatus in the claims.

BRIEF DESCRIPTION OF THE DRAWINGS

The accompanying drawings, which are incorporated in and constitute apart of this specification, illustrate embodiment of the present invention and, together with the description, serve to explain the objects, advantages and principles of the invention. In the drawings.

DETAILED DESCRIPTION OF THE PREFERRED EMBODIMENTS

Figure 1:
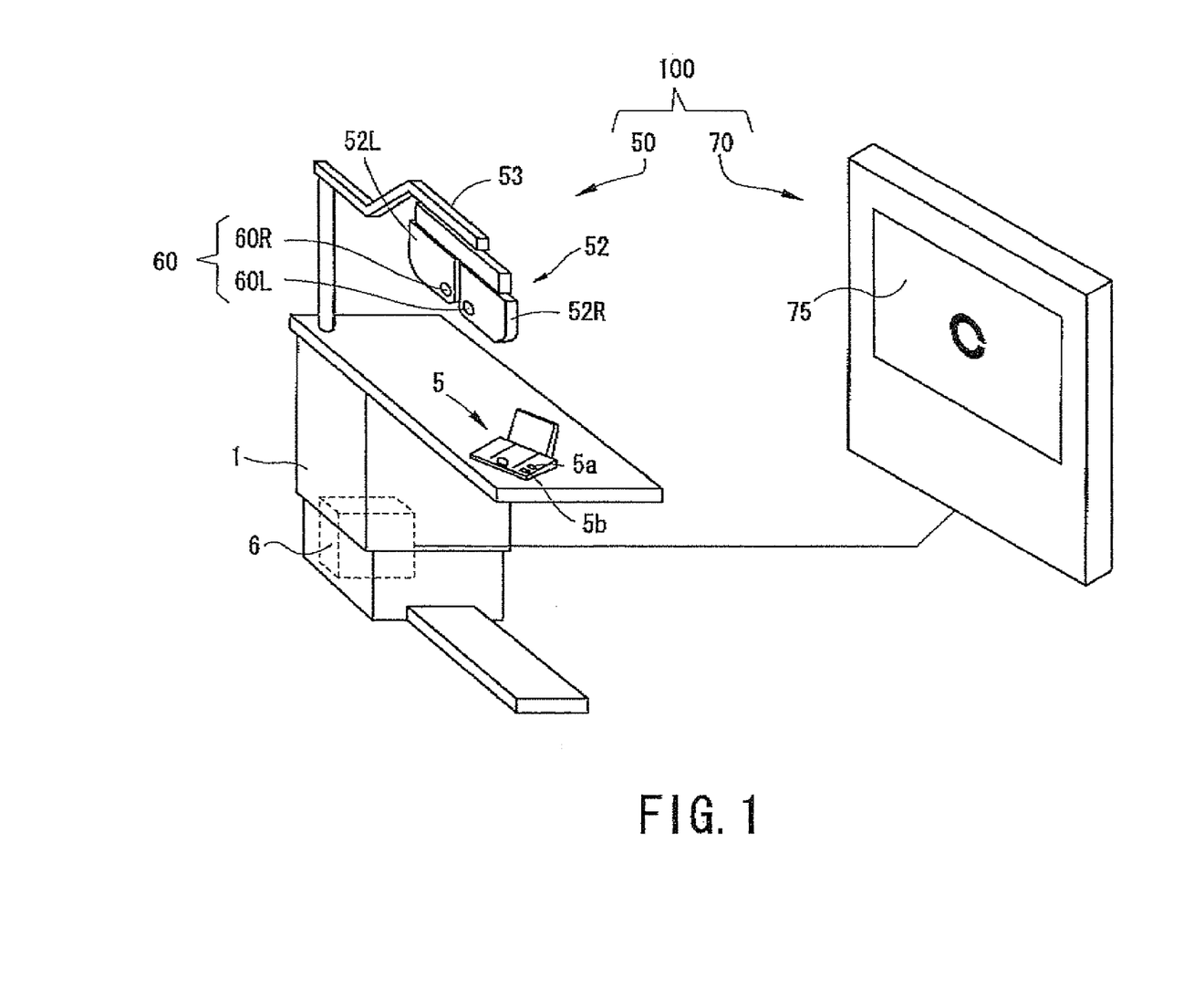
FIG. 1 is a view showing a schematic configuration of an optometric system including an optometric apparatus according to a preferred embodiment of the present invention.

A description of a preferred embodiment of an optometric apparatus embodied by the present invention will be provided below with reference to the accompanying drawings. FIG. 1 is a view showing a schematic configuration of an optometric system including the optometric apparatus according to the preferred embodiment of the present invention. An optometric system 100 includes an optometric apparatus 50 arranged to subjectively test (measure) visual performance of an examinee's eye, and the optometric apparatus 50 includes a lens chamber unit 52 (a pair of symmetric right and left lens chamber units 52R and 52L), and a supporting unit 53 arranged to suspend and support the lens chamber unit 52, and is fixed to a table 1 for an eye test. In the lens chamber unit 52, lens disks are held rotatably that include a lot of optical elements such as spherical lenses, cylindrical lenses and polarization plates that are disposed in a concyclic manner, and some of the optical elements are selected to be placed in a test window 60 (a right test window 60R and a left test window 60L) provided to the lens chamber unit 52. Selection of the optical elements to be placed in the test window 60 is performed through operation of a controller 5. The supporting unit 53 includes a space adjustment mechanism (including a convergence mechanism) for the lens chamber unit 52 that is arranged to change the space between the right test window 60R and the left test window 60L in accordance with the distance between the pupils of the examinee.

An optotype presenting apparatus 70 is arranged to present an optotype to the examinee's eye, and includes a presenting unit 75 on which the optotype is presented. The optotype presenting apparatus 70 is connected with the controller 5 via a relay unit 6, and selection of the optotype to be displayed on the presenting unit 75 is performed through the operation of the controller 5. The controller 5 includes a switch 5a for a visual acuity test and a switch 5b for a binocular vision test, and based on operation of the switch 5a or 5b, the optotype presenting apparatus 70 presents an optotype for the visual acuity test or an optotype for the binocular vision test on the presenting unit 75. The optotype presenting apparatus 70 is installed at a distance appropriate for the tests apart from the optometric apparatus 50 while positioned at a height almost same as the optometric apparatus 50.

It is to be noted that the optometric apparatus 50 has a configuration such that a binocular vision test can be performed by the optometric system 100 even if the optotype presenting apparatus 70 that is arranged to separate the optotype to be presented to the right and left eyes of the examinee using linearly polarized light is replaced with an optotype presenting apparatus 80 that is arranged to separate the optotype to be presented to the right and left eyes of the examinee using circularly polarized light.

Figure 2:
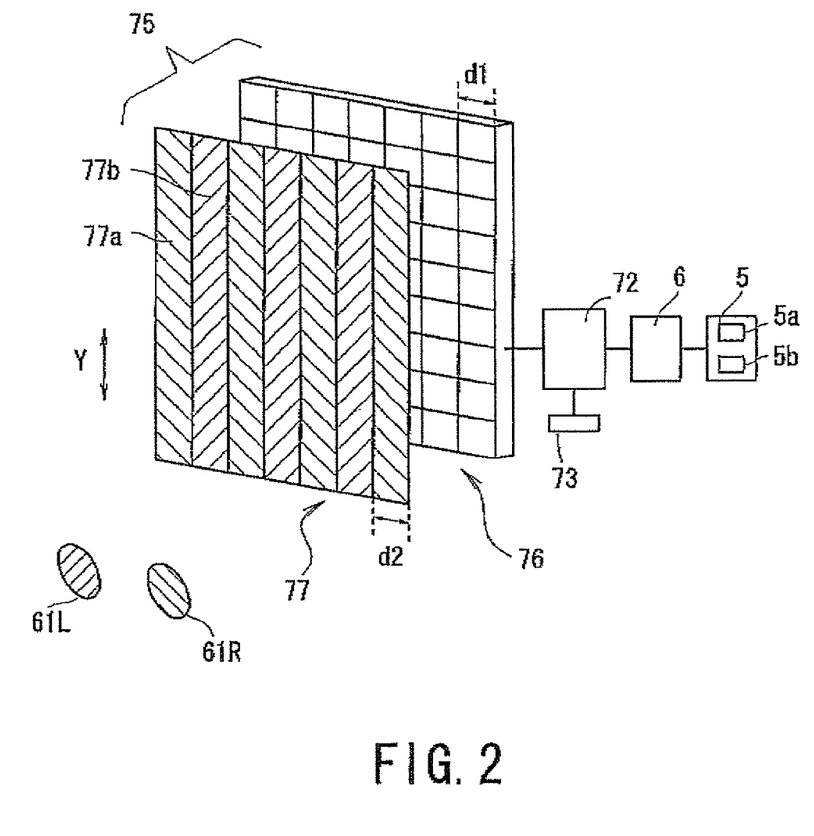
FIG. 2 is a view showing a configuration of a presenting unit and a control system of an optotype presenting apparatus.
Figure 3:
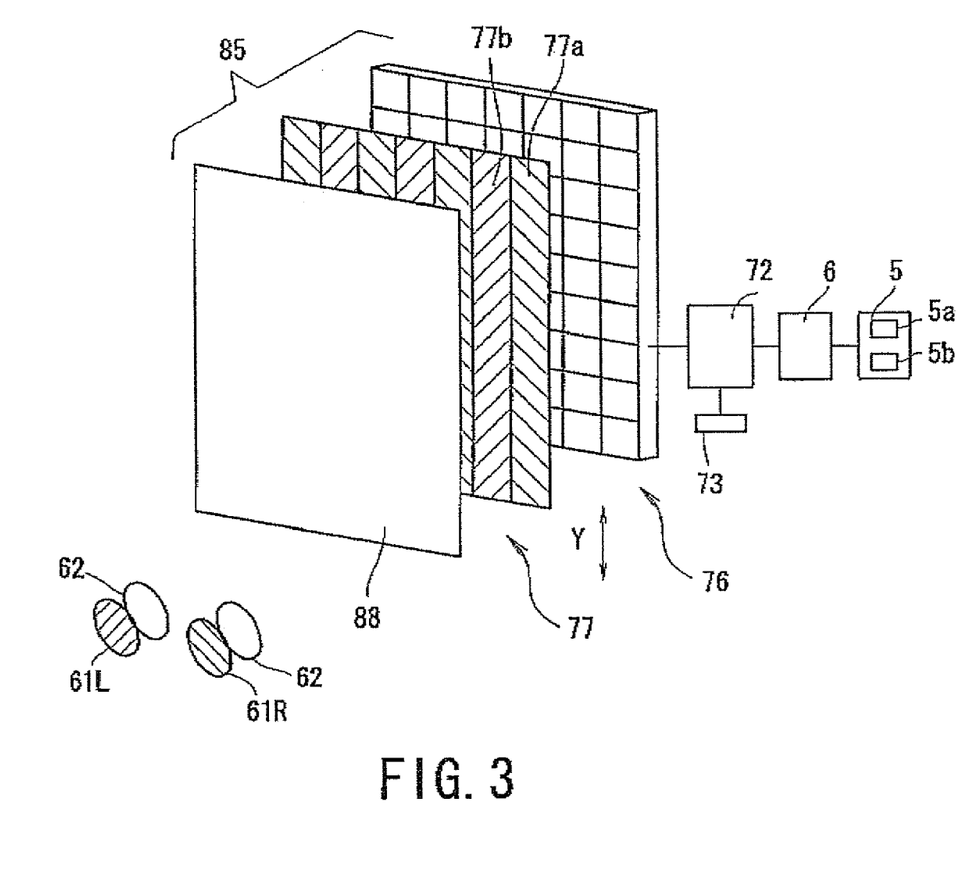
FIG. 3 is a view showing a configuration of a presenting unit and a control system of an optotype presenting apparatus.

Next, a description of the optotype presenting apparatuses 70 and 80 that are used in the preferred embodiment of the present invention will be provided. FIG. 2 is a view showing a configuration of the presenting unit 75 and a control system of the optotype presenting apparatus 70. FIG. 3 is a view showing a configuration of a presenting unit 85 and a control system of the optotype presenting apparatus 80.

The presenting unit 75 of the optotype presenting apparatus 70 includes a color liquid crystal display 76 and a sheet-like polarization optical member 77 that is disposed on (attached to) a front surface of the display 76. The polarization optical member 77 has a size as large as to cover at least an optotype presenting surface of the display 76. The display 76 is connected to a control unit 72. The control unit 72 includes a decoder circuit arranged to decode a command signal from the controller 5, and other components, and is arranged to read, based on the command signal, data on the optotype from a memory 73, and control the display 76 to display the optotype.

In the binocular vision test, polarization filters (polarization plates) 61R and 61L that have polarization axes perpendicular to each other are placed in the test windows 60R and 60L. The polarization axis of the polarization filter 61R for a right eye is oriented at 135 degrees, and the polarization axis of the polarization filter 61L for a left eye is oriented at 45 degrees.

The display 76 is arranged to emit linearly polarized light having a polarization axis (a polarization plane) in a predetermined direction (a vertical direction, a horizontal direction or an oblique direction of 45 or 135 degrees). In the preferred embodiment of the present invention, the linearly polarized light having the polarization axis in the vertical direction is emitted. The polarization optical member 77 has optical regions 77a and 77b that each have a linear shape extending in a longitudinal direction (a vertical direction: the arrow Y direction indicated in FIG. 2) corresponding to the size of a pixel of the display 76, and are alternately arranged in a lateral direction (a horizontal direction). A width d2 of each of the optical regions 77a and 77b corresponds to an integral multiple of a width d1 of one pixel of the display 76 (in the preferred embodiment of the present invention, one). The optical regions 77a and 77b are arranged to change the linearly polarized light having the polarization axes in the vertical direction that is emitted from the display 76 into linearly polarized light having polarization axes perpendicular to each other when transmitting the light. In the preferred embodiment of the present invention, the polarization optical member 77 has a function same as a half wavelength plate (a phase plate). The half wavelength plate has a function different from a polarization plate, and is arranged to rotate a vibration direction of incident light by 2×θ degree(s) when the incident light with a polarization plane enters at θ degree(s) with respect to a fast axis (or a slow axis) of the half wavelength plate. In other words, the half wavelength plate has, by inclination of the direction of its optically principal axis that is the fast axis (or the slow axis) with respect to the polarization axis direction of the incident light, a function of rotating a polarization axis direction (vibration direction) of the incident light and a property of being capable of maintaining light intensity of the incident light.

The optical regions 77a define optical regions for a right eye, and an optically principal axis direction of the optical regions 77a is oriented such that the incident light is changed into linearly polarized light having a polarization axis direction of 135 degrees that coincides with the polarization axis direction of the polarization filter 61R for the right eye. The optical regions 77b define optical regions for a left eye, and an optically principal axis direction of the optical regions 77b is oriented such that the incident light is changed into linearly polarized light having a polarization axis direction of 45 degrees that coincides with the polarization axis direction of the polarization filter 61L for the left eye. Thus, looking at the display on the presenting unit 75 through the polarization filters 61R and 61L placed respectively in front of the right and left eyes, the examinee visually perceives by the left eye only the light from the optical regions 77b that can pass through the polarization filter 61L, while the light from the optical regions 77a is blocked by the polarization filter 61L and is not visually perceived by the left eye. In contrast, the examinee visually perceives by the right eye only the light from the optical regions 77a that can pass through the polarization filter 61R, while the light from the optical regions 77b is blocked by the polarization filter 61R and is not visually perceived by the right eye. Different optotypes can be thus presented to the right and left eyes.

The presenting unit 85 of the optotype presenting apparatus 80 includes the display 76 and the polarization optical member 77 similarly to the presenting unit 75, and further includes a polarization optical member 88 that is disposed on (attached to) a front surface of the polarization optical member 77. The polarization optical member 88 has a size as large as to cover at least the polarization optical member 77. The polarization optical member 88 has a function of changing linearly polarized light into circularly polarized light, and has a function same as a quarter wavelength plate (a phase plate). The quarter wavelength plate has a polarization optical characteristic of changing linearly polarized light into circularly polarized light, and a function of providing a phase delay of 90 degrees to a predetermined component of a vector (a horizontal component or a vertical component) of polarized light. Thus, linearly polarized light that passes through the quarter wavelength plate is changed into circularly polarized light. In the preferred embodiment of the present invention, the quarter wavelength plate is disposed such that the linearly polarized light having the polarization axis direction of 135 degrees is changed into clockwise-rotated circularly polarized light when passing through the quarter wavelength plate, while the linearly polarized light having the polarization axis direction of 45 degrees is changed into counterclockwise-rotated circularly polarized light when passing through the quarter wavelength plate. Therefore, in the optotype presenting apparatus 80, the optotype for the right eye is made into the clockwise-rotated circularly polarized light while the optotype for the left eye is made into the counterclockwise-rotated circularly polarized light, and the different optotypes can be thus presented to the right and left eyes.

Meanwhile, at a side facing the examinee's eyes, quarter wavelength plates 62 are placed in front of the polarization filters 61R and 61L. A quarter wavelength plate has a function of providing a phase delay of 90 degrees to a predetermined component as described above, and thus has a function of changing circularly polarized light into linearly polarized light. The circularly polarized light is changed into the linearly polarized light by the quarter wavelength plates 62, and then the linearly polarized light is separated by their polarization axes with the use of the polarization filters 61R and 61L. The linearly polarized light having a polarization axis direction of 135 degrees enters the right eye, and the linearly polarized light having a polarization axis direction of 45 degrees enters the left eye. In the preferred embodiment of the present invention, the quarter wavelength plates 62 are disposed such that the clockwise-rotated circularly polarized light is changed into the linearly polarized light having the polarization axis direction of 135 degrees, while the counterclockwise-rotated circularly polarized light is changed into the linearly polarized light having the polarization axis direction of 45 degrees.

In the preferred embodiment of the present invention, the optical regions 77a and 77b have the configuration of each having the longitudinal linear shape, having the polarization axes perpendicular to each other, and being alternately arranged in the lateral direction; however, it is also preferable that the optical regions have a configuration of each having a lateral linear shape, having polarization axes perpendicular to each other, and being alternately arranged in the longitudinal direction. In addition, a liquid crystal display is used as the display 76; however, a display such as a plasma display, an organic EL display and an SED display can be also preferably used as the display 76. If light emitted from the display other than the liquid crystal display does not have a property of linearly polarized light, providing a polarization plate between the display and the polarization optical member will suffice.

It is also preferable that the polarization optical member 77 has the optical regions 77a made of polarization plates having a polarizing axis direction of 135 degrees and the optical regions 77b made of polarization plates having a polarizing axis direction of 45 degrees.

Figure 4:
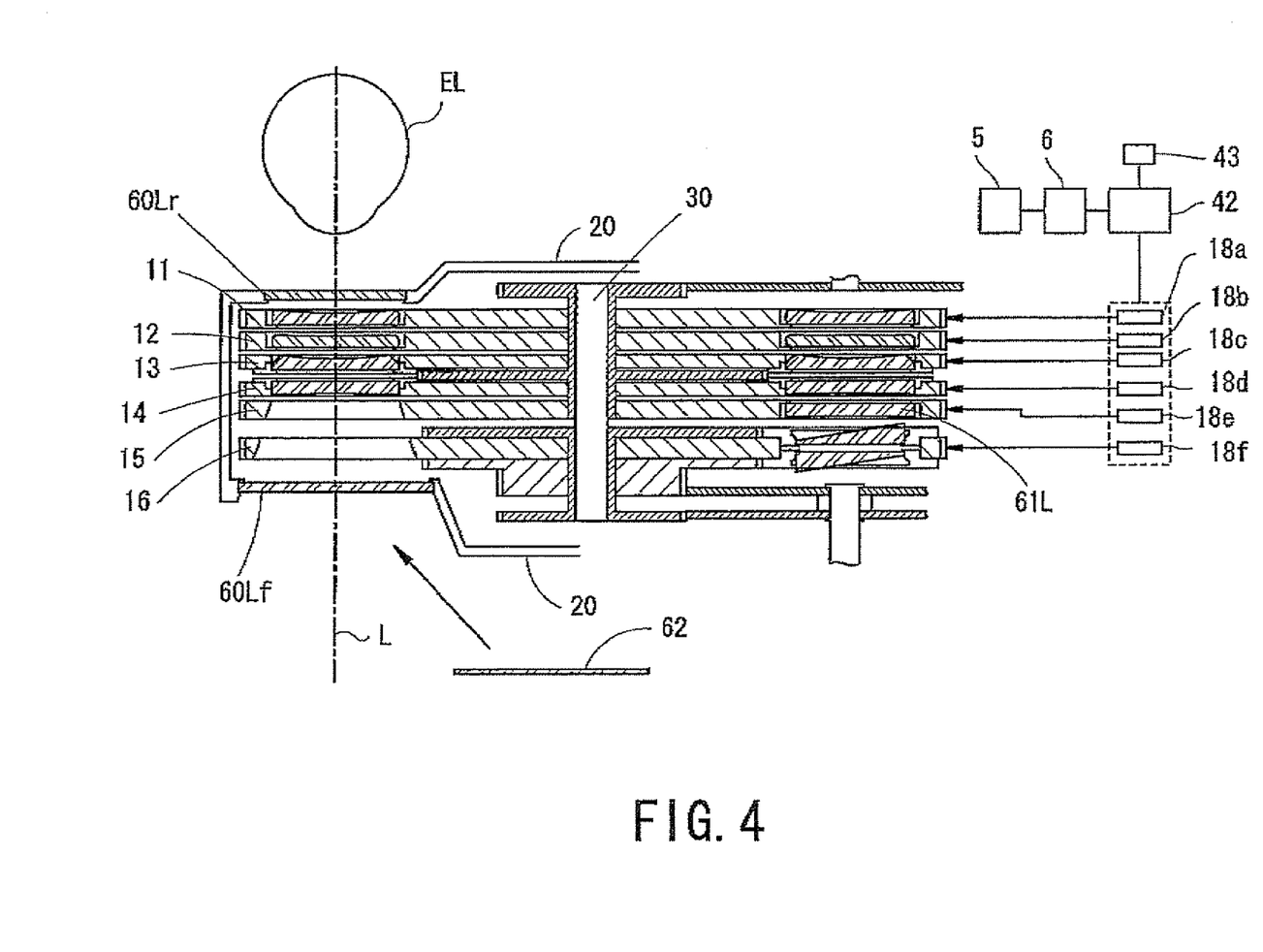
FIG. 4 is an overhead partial sectional view showing a left lens chamber unit and a view showing a control system of the optometric apparatus.

Next, a description of the optometric apparatus 50 will be provided. FIG. 4 is an overhead partial sectional view showing the left lens chamber unit 52L and a view showing a control system of the optometric apparatus 50. The lens chamber unit 52 is to be disposed such that its measurement optical axis L coincides with a visual axis of an examinee's left eye E (EL). In a cover 20 of the left lens chamber unit 52L, six lens disks 11 to 16 each including an opening and a plurality of optical elements are disposed rotatable about a shaft 30 as its center. The lens disk 11 is a disk for strong spherical lenses, the lens disk 12 is a disk for weak spherical lenses, the lens disk 13 is a disk for strong cylindrical lenses, the lens disk 14 is a disk for weak cylindrical lenses, the lens disk 15 is a first disk for auxiliary lenses, and the lens disk 16 is a second disk for auxiliary lenses, and the lens disks 11 to 16 are disposed in this order sequentially retreating from the eye E (EL). The lens disks 11 to 16 are rotated by corresponding motors 18a to 18f, and the optical elements to be disposed on the optical axis L are selected. The test window 60L includes a protective cover 60Lf at the side facing the examiner, and a protective cover 60Lr at the side facing the examinee. The protective covers 60Lf and 60Lr are arranged to prevent dust from entering the cover 20. The protective covers 60Lf and 60Lr are transparent members high in transparency so that the examinee can visually perceive the optotype through the optical members placed in the test window 60L.

The lens disk 15 for auxiliary lenses holds the polarization filter 61R or 61L in addition to the opening. The polarization filter 61L of the lens disk 15 of the left lens chamber unit 52L is held by the lens disk 15 so as to have a polarization axis direction of 45 degrees when placed in the test window 60L. In a similar manner, the polarization filter 61R of the lens disk 15 of the right lens chamber unit 52R is held by the lens disk 15 so as to have a polarization axis direction of 135 degrees when placed in the test window 60R.

The optometric apparatus 50 includes a control unit 42 arranged to control a main body, and a memory 43 arranged to store a control program and other data. The control unit 42 is connected with the controller 5 via the relay unit 6. The control unit 42 is arranged to drive and control the motors 18a to 18f to rotate the lens disks 11 to 16 to place desired optical elements in the test windows 60R and 60L.

The quarter wavelength plate 62 is attached in a detachable manner to the protective cover 60Lf. To be specific, the quarter wavelength plate 62 is made attachable and detachable by being provided with an adhesion property or a sticking property all over its surface. The adhesive force or sticking force of the quarter wavelength plate 62 is made in such a degree that the quarter wavelength plate 62 does not slip from the protective cover 60Lf when attached thereto while the quarter wavelength plate 62 is easily detached therefrom. The quarter wavelength plate 62 is attached in a detachable manner also to a protective cover 60Rf (not shown) at the side facing the examiner.

Having the configuration described above, the optometric apparatus 50 is adaptable to the binocular vision test both in the case of using the optotype presenting apparatus 70 and in the case of using the optotype presenting apparatus 80. To be specific, in the case of using the optotype presenting apparatus 70, while the quarter wavelength plates 62 are not attached to the protective covers 60Rf and 60Lf, the optotype presented by the optotype presenting apparatus 70 is separated by using the polarization filters 61R and 61L. In contrast, in the case of using the optotype presenting apparatus 80, while the quarter wavelength plates 62 are attached to the protective covers 60Rf and 60Lf, the optotype presented by the optotype presenting apparatus 80 is separated by using the quarter wavelength plates 62 and the polarization filters 61R and 61L.

It is to be noted that the quarter wavelength plates 62 have a size almost same as or larger than the polarization filters 61R and 61L, and almost same as or larger than the protective covers 60Rf and 60Lf. Thus, the quarter wavelength plates 62 cover the test windows 60R and 60L, and when the examinee looks at the optotype displayed on the optotype presenting apparatus 80 through the quarter wavelength plates 62 without the polarization filters 61R and 61L, the optotype is not separated. Therefore, unevenness does not easily show up in the optotype that the examinee looks at through the test windows 60R and 60L.

Figure 5:
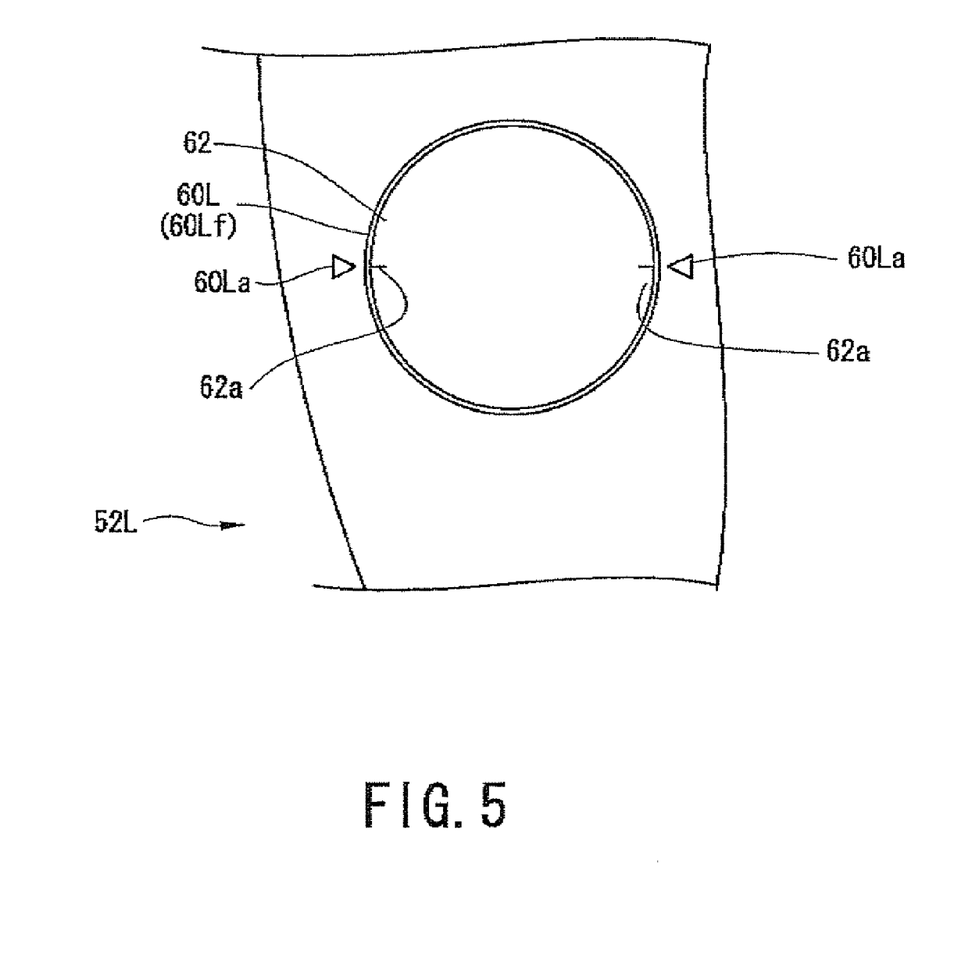
FIG. 5 is a view showing the vicinity of a test window of the left lens chamber unit that is seen from an examiner's side.

In addition, the quarter wavelength plate 62 is positioned such that the light changed into the circularly polarized light is changed into the light having the former polarization axis, and then attached to the protective cover 60Lf. FIG. 5 is a view showing the vicinity of the test window 60L of the left lens chamber unit 52L that is seen from the examiner's side. The quarter wavelength plate 62 includes first marks 62a for positioning. The test window 60L includes second marks 60La on its peripheral part at the side facing the examiner, the second marks 60La defining references with respect to which the first marks 62a are positioned. The first marks 62a are paired opposed marks, and the second marks 60La are paired opposed marks. Referring to the marks 62a and 60La, an operator performs positioning of the quarter wavelength plate 62 and attaches the quarter wavelength plate 62 to the protective cover 60Lf. The marks 62a have a shape such that they do not block the examinee's view when the examinee looks at the optotype through the test window 60L. The marks 60La suffice if they serve as a guide for positioning, and may be members such as screws for securing the protective cover 60Lf or may be provided to the protective cover 60Lf. Both the marks 6014a and the marks 62a may be provided in plurality of pairs. Both the marks 60La and the marks 62a may not have to be paired. The marks 60La may be provided to the test window 60L.

In a similar manner, the quarter wavelength plate 62 is attached also to the protective cover 60Rf of the right test window 60R at the side facing the examiner. Thus, even if the light that enters the test windows 60R and 60L is any circularly polarized light, the examinee can visually perceive it. To be specific, the clockwise-rotated circularly polarized light is changed into the linearly polarized light having the polarization axis direction of 135 degrees while the counterclockwise-rotated circularly polarized light is changed into the linearly polarized light having the polarization axis direction of 45 degrees, and the linearly polarized light reaches the examinee's eyes. If the polarization filters 61R and 61L are placed in the test windows 60R and 60L in addition to the quarter wavelength plates 62, only the linearly polarized light having the polarization axis direction of 135 degrees enters the right eye, and only the linearly polarized light having the polarization axis direction of 45 degrees enters the left eye. Thus, in a test performed using the optotype presenting apparatus 80 in which the circularly polarized light is used, different optotypes can be presented to the right and left eyes using the circularly polarized light. In addition, the resolution of the optotypes does not decrease in a visual acuity test and other tests.

Figure 6A:
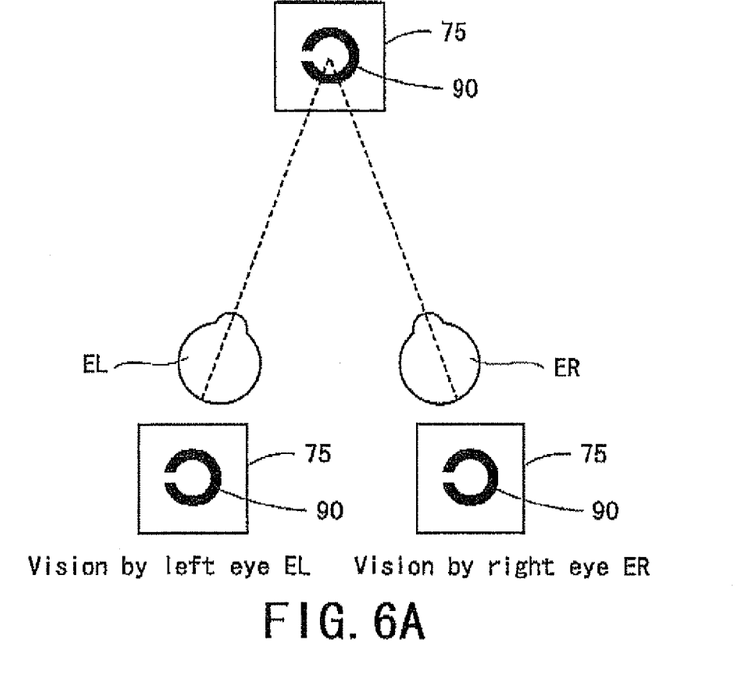
FIGS. 6A and 6B are views for illustrating a visual acuity test and a binocular vision test.
Figure 6B:
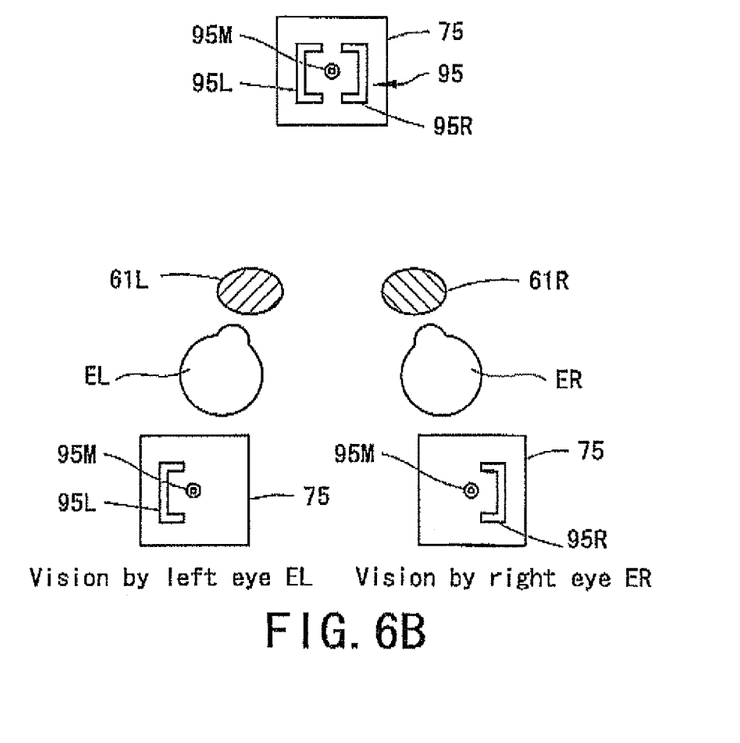
Figure 7A:
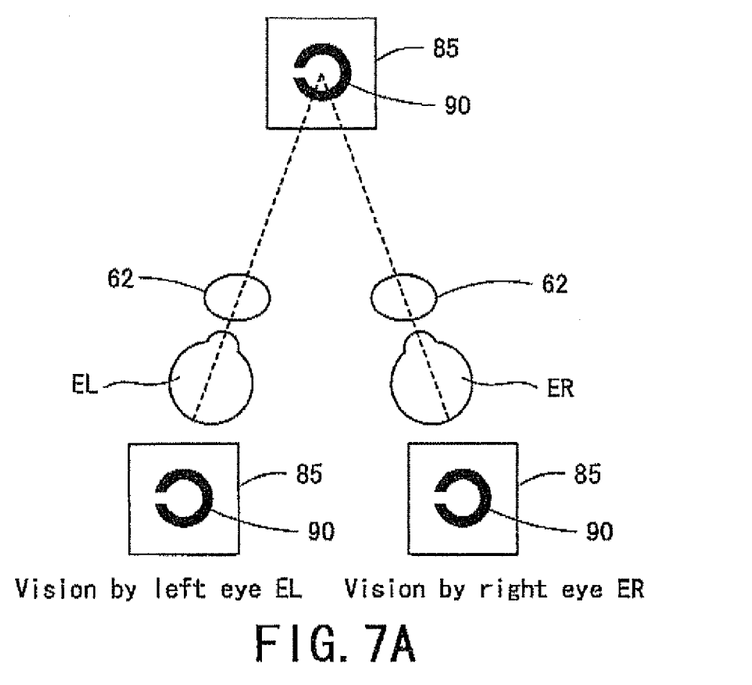
FIGS. 7A and 7B are views for illustrating a visual acuity test and a binocular vision test.
Figure 7B:
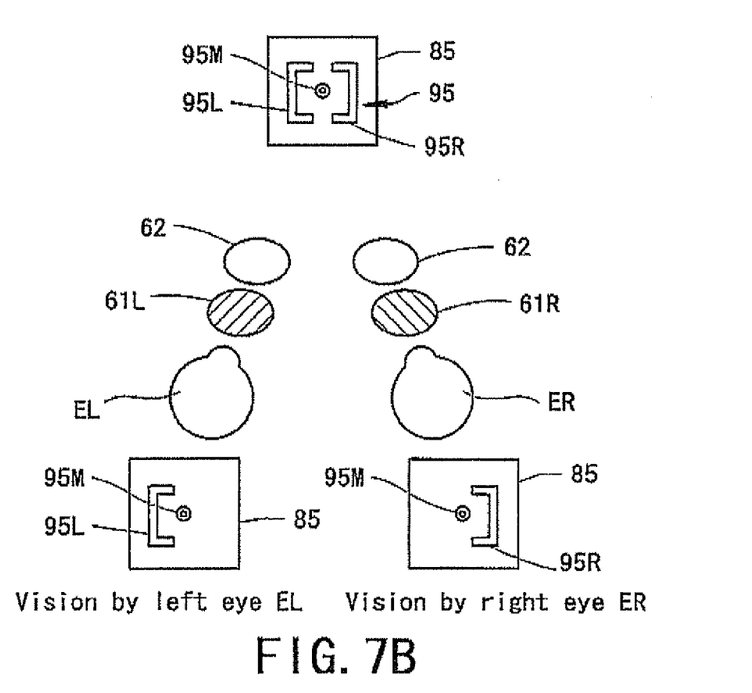

A description of a test using the optometric system 100 having the configuration as described above will be provided. FIGS. 6A and 6B are views for illustrating a visual acuity test and a binocular vision test using the optotype presenting apparatus 70. FIGS. 7A and 7B are views for illustrating a visual acuity test and a binocular vision test using the optotype presenting apparatus 80. In FIGS. 6A and 7A, illustrated are the visual acuity tests, and in FIGS. 6B and 7B, illustrated are the binocular vision tests. It is to be noted that the spherical lenses and other optical elements placed in front of the examinee's eyes are not shown.

Refractive power of a right eye ER and refractive power of a left eye EL (e.g., sphere power, astigmatic power, an astigmatic axis) of the examinee are measured by operating the optometric apparatus 50 and the optotype presenting apparatus 70 or 80. The examiner presses the switch 5a and performs the visual acuity test. To be specific, the examiner operates the controller 5 to present an optotype 90 for a visual acuity test (e.g., a Landort-ring optotype) on the optotype presenting apparatus 70 or 80, selects to place the optical elements in the test windows 60R and 60L, and measures the refractive power of the examinee's eyes.

The polarization filters 61R and 61L are not used in the visual acuity test using the optotype presenting apparatus 70 or 80, and the optotype 90 is visually perceived by the right eye ER and left eye EL. The control unit 72 forms the optotype 90 in the optical regions 77a and 77b of the presenting unit 75 or 85, so that the optotype 90 can be formed at a resolution the display 76 has, which allows a small optotype for a visual acuity such as 2.0 to be presented to the examinee's eyes.

Next, the examiner presses the switch 5b and performs the binocular vision test (an aniseikonia test in the preferred embodiment of the present invention). To be specific, the examiner operates the controller 5 to present an optotype 95 for an aniseikonia test on the optotype presenting apparatus 70 or 80, and places the polarization filters 61R and 61L in the test windows 60R and 60L. A fixation target 95M and a right optotype 95R of the optotype 95 are visually perceived by the right eye ER. In contrast, the fixation target 95M and a left optotype 95L of the optotype 95 are visually perceived by the left eye EL. By checking a deviation in vision by the examinee between the right optotype 95R and the left optotype 95L, the examiner checks up for strabismus of the examinee's eyes.

In the aniseikonia test using the optotype presenting apparatus 70, the control unit 72 forms the fixation target 95M and the right optotype 95R in given regions of the display 76 that correspond to the optical regions 77a, and forms the fixation target 95M and the left optotype 95L in given regions of the display 76 that correspond to the optical regions 77b. The fixation target 95M and the right optotype 95R have a polarization axis direction of 135 degrees, and the fixation target 95M and the left optotype 95L have a polarization axis direction of 45 degrees. Looking at the presenting unit 75 through the polarization filter 61R having the polarization axis direction of 135 degrees, the right eye ER visually perceives the fixation target 95M and the right optotype 95R (the left optotype 95L is not visually perceived). In contrast, looking at the presenting unit 75 through the polarization filter 61L having the polarization axis direction of 45 degrees, the left eye EL visually perceives the fixation target 95M and the left optotype 95L (the right optotype 95R is not visually perceived). In this manner, the optotype 95 is presented to the right and left eyes, and the aniseikonia test is performed.

Meanwhile, in the aniseikonia test using the optotype presenting apparatus 80, the control unit 72 forms the fixation target 95M and the right optotype 95R in given regions of the display 76 that correspond to the optical regions 77a, and forms the fixation target 95M and the left optotype 95L in given regions of the display 76 that correspond to the optical regions 77b. Linearly polarized light of the fixation target 95M and the right optotype 95R that has a polarization axis direction of 135 degrees is changed into clockwise-rotated circularly polarized light by the polarization optical member 88, while linearly polarized light of the fixation target 95M and the left optotype 95L that has a polarization axis direction of 45 degrees is changed into counterclockwise-rotated circularly polarized light by the polarization optical member 88. The clockwise-rotated circularly polarized light of the fixation target 95M and the right optotype 95R is changed into linearly polarized light having a polarization axis direction of 135 degrees by the quarter wavelength plate 62 and reaches the polarization filter 61R, while the counterclockwise-rotated circularly polarized light of the fixation target 95M and the left optotype 95L is changed into linearly polarized light having a polarization axis direction of 45 degrees by the quarter wavelength plate 62 and reaches the polarization filter 61L. Looking at the presenting unit 85 through the polarization filter 61R having the polarization axis direction of 135 degrees, the right eye ER visually perceives the fixation target 95M and the right optotype 95R (the left optotype 95L is not visually perceived). In contrast, looking at the presenting unit 85 through the polarization filter 61L having the polarization axis direction of 45 degrees, the left eye EL visually perceives the fixation target 95M and the left optotype 95L (the right optotype 95R is not visually perceived). In this manner, the optotype 95 is presented to the right and left eyes, and the aniseikonia test is performed.

As described above, having the configuration that the quarter wavelength plates 62 are placed in front of the polarization filters 61R and 61L in the attachable and detachable manner, the optometric system 100 can perform the binocular vision test by presenting the optotype for the binocular vision test to the right and left eyes, whether the optotype presenting apparatus included therein is the apparatus 70 in which the linearly polarized light is used or the apparatus 80 in which the circularly polarized light is used. In addition, in the binocular vision tests using the optotype presenting apparatuses 70 and 80, the operation of the controller 5 is identical, so that there is no need to change the control program for the optometric apparatus 50, and only attaching or detaching the quarter wavelength plates 62 allows the optometric apparatus 50 to be easily compatible with either of the optotype presenting apparatuses 70 and 80. In addition, there is no need to provide the polarization filters and the quarter wavelength plates to the lens disks in the optometric apparatus, which does not cause upsizing of the optometric apparatus nor an increase in cost.

In the preferred embodiment of the present invention, the quarter wavelength plates (polarization optical members) are attached or stuck to the protective covers 60Rf and 60Lf at the side facing the examiner; however, it is also preferable that the protective covers at the side facing the examiner are replaced with the quarter wavelength plates (polarization optical members). In other words, the protective covers at the side facing the examiner may be switched between the member having no polarization optical characteristic and the member having a polarization optical characteristic.

In the preferred embodiment of the present invention, it is also preferable that the test windows 60L and 60R do not include the marks 60La and marks 60Ra (not shown), and that the quarter wavelength plates 62 do not include the marks 62a. In this case, by presenting the optotype for the binocular vision test on the optotype presenting apparatus 80, the operator performs positioning of the quarter wavelength plates 62 by a visual check through the test windows 60R and 60L. For example, the positioning of the quarter wavelength plates 62 is performed such that the optotype for the left eye can be visually perceived through the left test window 60L while the optotype for the right eye cannot be visually perceived through the left test window 60L. In addition, the positioning of the quarter wavelength plates 62 is performed such that the optotype for the right eye can be visually perceived through the right test window 60R while the optotype for the left eye cannot be visually perceived through the right test window 60R.

In the preferred embodiment of the present invention, the optometric apparatus 50 is of the electric motor-driven type; however, the optometric apparatus 50 may be of the manual-operated type. In this case, the operation of the optotype presenting apparatus is performed with the use of a controller for the optotype presenting apparatus.

The foregoing description of the preferred embodiment of the invention has been presented for purposes of illustration and description. It is not intended to be exhaustive or to limit the invention to the precise form disclosed, and modifications and variations are possible in the light of the above teachings or may be acquired from practice of the invention. The embodiment chosen and described in order to explain the principles of the invention and its practical application to enable one skilled in the art to utilize the invention in various embodiments and with various modifications as is suited to the particular use contemplated. It is intended that the scope of the invention be defined by the claims appended hereto, and their equivalents.

What is claimed is:

1. An optometric apparatus for a subjective binocular visual performance test, the apparatus comprising
   right and left test units comprising:
   right and left housings;
   a plurality of optical elements disposed in each of the right and left housings;
   right and left test windows provided respectively to the right and left housings, in which desired optical elements selected from the optical elements are to be placed and through the selected optical elements, an optotype is presented to examinee's right and left eyes by an optotype presenting apparatus;
   right and left polarization plates having polarization axes perpendicular to each other, and arranged to be placed respectively in the right and left test windows; and
   right and left protective covers arranged to be placed respectively in the right and left test windows at a side facing the optotype presenting apparatus, and having polarization optical characteristics of changing circularly polarized light that passes through the right and left protective covers into linearly polarized light having polarization axes perpendicular to each other.

2. The optometric apparatus according to claim 1, wherein the right and left protective covers each comprise a transparent member and a polarization optical member, the polarization optical members having polarization optical characteristics same as those of the right and left protective covers.

3. The optometric apparatus according to claim 2, wherein the polarization optical members are attached to the transparent members in a detachable manner.

4. The optometric apparatus according to claim 3, wherein the polarization optical members each comprise a first mark for positioning with which a rotation direction of the circularly polarized light that passes through the polarization optical member is checked, and the test windows or peripheral parts of the test windows each comprise a second mark for positioning, the second marks corresponding to the first marks.

5. The optometric apparatus according to claim 1, wherein the right and left protective covers are attached respectively to the right and left test windows in a detachable manner.

6. The optometric apparatus according to claim 5, wherein the right and left protective covers each comprise a first mark for positioning with which a rotation direction of the circularly polarized light that passes through the protective cover is checked, and the test windows or peripheral parts of the test windows each comprise a second mark for positioning, the second marks corresponding to the first marks.

* * * * *